United States Patent [19]

Cabelli et al.

[11] 4,332,786

[45] Jun. 1, 1982

[54] METHOD AND COMPOSITION FOR VITAMIN B-12 ASSAY

[75] Inventors: Michael D. Cabelli, Watertown; Ernest V. Groman, Brookline, both of Mass.

[73] Assignee: Baxter Travenol Laboratories, Inc., Deerfield, Ill.

[21] Appl. No.: 150,022

[22] Filed: May 15, 1980

[51] Int. Cl.³ .................. G01N 33/54; G01N 33/58; G01N 33/60

[52] U.S. Cl. .................................. 424/1; 23/230 B; 424/12

[58] Field of Search .................... 424/1, 12; 23/230 B

[56] References Cited

U.S. PATENT DOCUMENTS

| | | | |
|---|---|---|---|
| 3,937,799 | 2/1976 | Lewin et al. | 424/1 |
| 4,028,465 | 6/1977 | Lewin et al. | 421/1 |
| 4,146,602 | 3/1979 | Gutcho et al. | 424/1 |
| 4,188,189 | 2/1980 | Allen | 424/1 |

FOREIGN PATENT DOCUMENTS 2011070 7/1979 United Kingdom .................... 424/1

OTHER PUBLICATIONS

Ithakissios, et al. "Clin. Chem." 26(2): 323–326, Feb. 1980.

"Chemical Abstracts" 87:806185 (1977).

Fox, et al., *Introduction to Protein Chemistry*, pp. 304–326 (1957).

*Primary Examiner*—Christine M. Nucker
*Attorney, Agent, or Firm*—Paul C. Flattery; Lawrence W. Flynn; Max D. Hensley

[57] ABSTRACT

The binding of vitamin B-12 by natural substances in samples assayed for vitamin B-12 is reduced by heating the test sample in an alkaline buffer comprising thioglycerol and denaturing agent having the formula $(R)_2NC(A)N(R)_2$, wherein R is hydrogen or lower alkyl and A is oxygen or hydroxyl.

12 Claims, No Drawings

METHOD AND COMPOSITION FOR VITAMIN B-12 ASSAY

BACKGROUND OF THE INVENTION

This invention relates to methods for diagnosing vitamin B-12 deficiency. In particular, it is concerned with those methods for determining B-12 which include a step of separating the vitamin from substances present in body fluids which reversibly bind the vitamin.

Vitamin B-12 is transported in body fluids such as blood plasma by a group of $\alpha$ and $\beta$ globulins including transcobalamins I, II and III to which the vitamin is reversibly bound. These substances are hereinafter referred to as sample binding proteins. Presently favored vitamin B-12 assays treat the samples to release the vitamin from these binding proteins, usually by way of the concomitant irreversible denaturation of the proteins. The sample is then incubated with labelled vitamin B-12 and a limited amount of a specific vitamin B-12 binding protein such as intrinsic factor, whereby the labelled and sample vitamin compete for binding sites on the binding protein in proportion to their relative concentration. This specific binding protein is generally derived from a different source than the sample binding proteins; such specific binding proteins are well known and are characterized by high affinity and specificity for vitamin B-12. They are hereinafter referred to as reagent binding proteins. The mixture is then treated, to separate the protein bound and unbound vitamin, e.g. by adsorption of the free vitamin onto charcoal by immune or precipitation of the bound vitamin and followed by centrifugation. Either fraction is then assayed for the amount of label it contains.

The vitamin must be released from the sample binding proteins. If it is not, then that proportion of the vitamin which remains bound to the sample proteins will not be free to participate in the competition with labelled vitamin for the reagent binding protein. The result will be an incorrectly low value for the patient's total vitamin B-12. This competitive vitamin binding by test sample endogenous protein is henceforth termed sample binding. The amount of sample binding is determined by conducting the vitamin assay in the conventional fashion but in the absence of the reagent binding protein; any labelled vitamin which is located in the fraction in which the reagent binding protein would be normally found is a function of sample binding.

It is known to release a part of the bound vitamin by heating the test samples at 100° C. to denature the sample binding proteins. However, Lee-Own et al. disclose that heat denaturing the samples excessively, i.e., heating at 100° C. for more than about 5 minutes, will reinstate a portion of the binding activity. According to these authors protein reactivation can be prevented by adding dithiothreitol to the sample during the heating step.

We have found that heating in the presence of dithiothreitol fails to entirely eliminate sample binding in vitamin B-12 assays. For example, in our method we commonly encounter residual sample binding on the order of 20–25% when heat alone is used, and from 9–12% after heating with dithiothreitol.

OBJECTS OF THE INVENTION

Accordingly, it is an object of this invention to provide a method and composition for reducing the level of sample binding in methods for determining vitamin B-12.

It is a further object to provide a composition for achieving the foregoing object which will not significantly adversely affect the capacity or affinity for vitamin B-12 of the reagent binding protein.

SUMMARY OF THE INVENTION

The invention constitutes an improvement in assays for vitamin B-12 wherein a sample which contains the vitamin bound to sample binding proteins is heat treated to release the vitamin, the improvement comprising contacting the sample binding protein with a denaturing agent having the formula $(R)_2NC(A)N(R)_2$, wherein R is hydrogen or lower alkyl and A is oxygen or hydroxyl.

An additional embodiment of the invention constitutes a further improvement in assays for vitamin B-12 wherein a sample which contains the vitamin bound to sample binding proteins is heat treated to release the vitamin, the improvement comprising conducting the heat treatment in the presence of thioglycerol. The denaturing agent may also be used in conjunction with thioglycerol.

Also provided is a composition comprising dithiothreitol or thioglycerol and a denaturing agent having the formula $(R)_2NC(A)N(R)_2$, wherein R is hydrogen or lower alkyl and A is oxygen or hydroxyl. An alternate or supplemental composition for use in the novel method described herein comprises a vitamin B-12 tracer and the above-described denaturing agent.

DESCRIPTION OF THE PREFERRED EMBODIMENTS

The denaturing agent $(R)_2NC(A)N(R)_2$ is preferably urea, although its equilibrium under the assay conditions may result in the in situ formation of a proportion of pseudourea, i.e., where A is hydroxyl. The nitrogen atoms of the agent may also be substituted with lower alkyl groups having from 1 to 3 carbon atoms, ordinarily methyl, but it is generally desirable that no more than one R group be lower alkyl.

The mode of action of the denaturing agent is not understood. It may act to release vitamin B-12 from tenacious heat-denatured sample binding proteins or to prevent the reassociation of vitamin B-12 with the proteins after they are cooled to room temperature before further assay steps.

Since heat is a highly effective protein denaturing agent it was surprising that another denaturing agent would be effective in preventing any further residual sample binding of vitamin B-12. It was even more surprising that guanidine, a protein denaturant related in structure to urea, was entirely ineffective at achieving our goals. Also ineffective in reducing sample binding was 0.0001 to 0.1% Triton X-100 detergent, 1% polyethlene glycol, 0.1% 8-anilino-1-napthalene sulfonic acid, catalase and phenolphthalein. Percentages were by weight in the assay mixture.

It was additionally surprising that the denaturing agent did not inhibit the binding of vitamin B-12 by reagent binding proteins, particularly intrinsic factor. Thus, the agent will not interfere in the assay even though it is carried through from the heat treating step.

The particular denaturing agent to select for a given set of assay conditions and the optimal concentration thereof will depend upon a number of factors. The nature of the test sample is one. For example, high levels of high affinity, high capacity, endogenous binding proteins dictate larger amounts of agent. The gross protein concentration, ionic strength and pH of the test sample also will affect the optimum concentration of the agent. Routine experimentation well within the purview of the skilled artisan can be used to determine the identity and concentration of the agent needed to secure the maximum release of vitamin B-12 from the sample being treated.

Another factor is the effect of the agent and its concentration on the specific binding protein used in the subsequent specific binding assay. While intrinsic factor is comparatively insensitive to the denaturing agents described herein, use of excessive agent will only serve unnecessarily to increase the amount of specific binding protein required to conduct the assay. Thus, routine experimentation is desirable to arrive at the concentration of agent at which the specific binding protein can bind the most vitamin B-12.

The optimal concentration of agent to be used throughout the assay will generally be balanced between that which reduces the vitamin binding by heat sample binding proteins and that at which maximum vitamin binding by specific binding protein occurs. Generally, a midpoint between the two concentrations is selected, although it is preferable to skew the choice more towards the point of maximum vitamin disassociation from the sample binding proteins.

A representative suitable concentration range for the denaturing agent is about from 0.1 to 0.8 M, with about 0.35 M being preferable. This concentration range is not critical. This concentration is that which is established in the sample while it is being heat treated; the concentration in the subsequent analytical steps will be slightly lower, on the order of about 10%, because of the addition of the specific binding protein solution. The composition which comprises the vitamin B-12 tracer and the denaturing agent may contain an amount of agent which will yield a concentration within the above range when added or reconstituted into the sample. Obviously, since the agent may be dry or in aqueous solution, and in a quantity suitable for any number of analytical determinations, the amount of agent in the composition will vary widely.

The denaturing agent-containing compositions may also contain dithiothreitol or thioglycerol. Dithiothreitol is known for heat-treating samples for vitamin B-12 assay, and the concentrations employed by the prior art are suitable here as well. Typically, sufficient dithiothreitol will be employed in the composition to produce a 0.1% concentration during the heat treatment.

Thioglycerol is preferred over dithiothreitol. Thioglycerol is more storage stable and less expensive than dithiothreitol, yet has been found to be at least as effective at reducing the nonspecific binding of the vitamin. The thioglycerol concentration selected for use in the heat treatment step should be balanced between that which maximizes the release of vitamin from sample binding proteins while minimizing specific binding protein inhibition. A concentration range of about from 0.05% to 0.5% by weight is generally satisfactory with about 0.3% being preferred. The concentration in reagents should be calculated to yield a concentration within this range upon use.

Sample binding levels half that previously attainable when heat treating with dithiothreitol have been attained. Typically, no more than 4% nonspecific binding has been encountered when using the denaturing agent and thioglycerol during heat treating.

The denaturing agent may be supplied as a component in kits for the specific binding assay of vitamin B-12. These kits conventionally contain a specific binding protein, e.g., purified or unpurified intrinsic factor, labelled vitamin B-12, e.g, as cyano[57Co]cobalamin, standards and controls, a buffer solution and a reagent, e.g, charcoal, for separating free labelled and sample vitamin B-12 from that which is bound to the specific binding protein. The denaturing agent is generally supplied as a component of the buffer solution with which the samples and standards are mixed prior to heat treatment. A separate solution of thioglycerol or dithiothreitol is usually supplied, but it may be combined with the solution of denaturing agent if it is to be used within several days. Alternatively, one or both of the denaturing agent or either thioglycerol or dithiothreitol can be combined with the tracer, in either dry or aqueous form, as described above. The preferred tracer is radiolabelled with cobalt 57, but it is possible to employ other labels such as radioiodine, enzymes, stable free radicals or fluorescent groups.

The prior art has conventionally combined the reagents and method for folate assay with those for vitamin B-12 determinations. The method described herein for vitamin B-12 assay is compatible with such methods for folate, and the compositions herein described may also contain reagents for folate assay, e.g., folate tracers and milk binding protein. However, it is preferred to optimize by routine experimentation the concentrations of denaturing agent and thioglycerol so as to minimize the impact on the folate determination.

The invention will be more fully understood upon consideration of the following example.

EXAMPLE 1

The following reagents were provided for the assay of vitamin B-12 in human serum:
(1) a borate buffered solution of 0.4 M urea at pH 9.2;
(2) a 5% by weight thioglycerol solution;
(3) an aqueous solution of intrinsic factor;
(4) lyophilized cyano[57Co]cobalamin;
(5) standards of 0, 75, 150, 300, 600, 1200 and 2400 pg vitamin B-12/ml; and
(6) charcoal tablets.

In the practice of the assay 130 ml of the buffered urea solution is used to reconstitute the tracer and the solution then thoroughly mixed with 8 ml of thioglycerol solution. Duplicate polypropylene tubes are labelled for each standard and test sample and for determination of residual sample binding. 100 microliters of each standard and test sample are added to the appropriate tubes. 100 microliter of vitamin B-12 blank solution are pipetted into each of the sample binding tubes. 1.0 ml of the urea, thioglycerol and tracer-containing buffer solution are mixed with the contents of each tube, the tubes capped and incubated in a boiling water bath for 15 minutes. The tubes are cooled to room temperature after which 100 microliters of intrinsic factor solution are mixed with the contents of all tubes except for the sample binding tubes. After incubating for 30 minutes on charcoal tablet is dispensed in each tube, incubated for 10 minutes, centrifuged for 10 minutes and the supernatant decanted from each tube into empty counting tubes. The radioactivity contained in each tube is then determined and the data handled in conventional fashion.

We claim:

1. In a method for determining vitamin B-12 wherein a sample which contains the vitamin bound to sample binding proteins is heat treated to release the vitamin, the improvement comprising contacting the sample binding protein during the heat treatment with a denaturing agent having the formula $(R)_2NC(A)N(R)_2$, wherein R is hydrogen or lower alkyl and A is oxygen or hydroxyl.

2. The method of claim 1 wherein the sample binding protein is contacted with the denaturing agent by mixing the agent with the sample prior to the heat treatment.

3. The method of claim 1 wherein the agent is urea.

4. The method of claim 3 wherein the concentration of urea is about from 0.1 to 0.8 M.

5. The method of claim 1 wherein the sample binding protein is also contacted with dithiothreitol.

6. The method of claim 1 wherein the sample binding protein is also contacted with thioglycerol.

7. In a method for determining vitamin B-12 wherein a sample which contains the vitamin bound to sample binding proteins is heat treated to release the vitamin, the improvement comprising conducting the heat treatment in the presence of thioglycerol.

8. The method of claim 7 wherein the thioglycerol concentration is about from 0.05% to 0.5% by weight.

9. A composition comprising dithiothreitol or thioglycerol and a denaturing agent having the formula $(R)_2NC(A)N(R)_2$, wherein R is hydrogen or lower alkyl and A is oxygen or hydroxyl.

10. The composition of claim 9 further comprising labelled vitamin B-12.

11. A composition comprising labelled vitamin B-12 and a denaturing agent having the formula $(R)_2NC(A)N(R)_2$, wherein R is hydrogen or lower alkyl and A is oxygen or hydroxyl.

12. The composition of claims 9 or 11 which is dry.

* * * * *